United States Patent [19]

Andrews

[11] 4,368,330

[45] Jan. 11, 1983

[54] DERIVATIVES OF L-ASCORBIC ACID AND D-ERYTHORBIC ACID

[75] Inventor: Glenn C. Andrews, Waterford, Conn.

[73] Assignee: Pfizer Inc., New York, N.Y.

[21] Appl. No.: 259,206

[22] Filed: Apr. 30, 1981

[51] Int. Cl.$^3$ ............................................. C07D 407/04
[52] U.S. Cl. ...................................... 549/315; 549/316
[58] Field of Search ......................... 260/343.7, 343.6; 549/315, 316

[56] References Cited

U.S. PATENT DOCUMENTS 2,590,067 3/1952 Pecherer .......................... 260/343.7
4,043,937 8/1977 Kiss et al. ............................ 252/407

OTHER PUBLICATIONS

Müller and Reichstein, Helv. Chim. Acta 21, 273–277 (1938).
Bock, Lundt and Pedersen, Carbohydrate Research 63, 313–319 (1979).

Primary Examiner—Norma S. Milestone
Attorney, Agent, or Firm—Charles J. Knuth; Peter C. Richardson; Harold W. Ordway

[57] ABSTRACT

5,6-Anhydro-L-ascorbic acid, 5,6-anhydro-D-erythorbic acid and salts thereof are disclosed. Such compounds are useful intermediates in the preparation of 6-deoxy-6-substituted-L-ascorbic acid and 6-deoxy-6-substituted-D-erythorbic acid, which are useful as antioxidants. Novel 6-deoxy-6-substituted-L-ascorbic and -D-erythorbic acid derivatives are also disclosed.

4 Claims, No Drawings

4,368,330

DERIVATIVES OF L-ASCORBIC ACID AND D-ERYTHORBIC ACID

BACKGROUND OF THE INVENTION

This invention relates to novel L-ascorbic acid and D-erythorbic acid derivatives useful in the preparation of 6-deoxy-6-substituted-L-ascorbic and -D-erythorbic acids and salts thereof. The 6-deoxy-6-substituted compounds are useful as antioxidants.

While L-ascorbic acid and D-erythorbic acids are useful as antioxidants they are relatively labile in aqueous solution, especially under acid conditions. In efforts to provide antioxidants of improved stability, 6-deoxy-6-halo-L-ascorbic acid and 6-deoxy-6-halo-d-erythorbic acid have been prepared, see U.S. Pat. No. 4,043,937 and Carbohydrate Research 68, 313 (1979). 6-Deoxy-L-ascorbic acid has also been prepared, see H. Müller and T. Reichstein, Helv. Chim. Acta 21, 273 (1938).

SUMMARY OF THE INVENTION

The present invention relates to novel intermediates of the formula

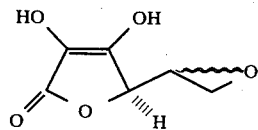

and salts thereof. It will be understood that, depending on the chirality of the epoxide group at the $C_5$ position, formula I represents either 5,6-anhydro-L-ascorbic acid or 5,6-anhydro-D-erythorbic acid.

The present invention also includes novel 6-deoxy-6-substituted-L-ascorbic acid and 6-deoxy-6-substituted-D-erythorbic acid derivatives of the formula

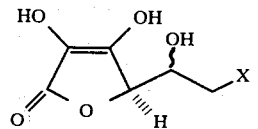

wherein X is amino, azido, phenoxy, thiophenoxy or thioalkoxy of 1 to 3 carbon atoms and the salts thereof. Preferably X is amino. The compounds of Formula II are useful as antioxidants.

The compounds of Formula I are useful as intermediates for the preparation of the novel compounds of formula II and also for preparation of known 6-deoxy-6-substituted-L-ascorbic acid and 6-deoxy-6-substituted-D-erythorbic acid derivatives, such as 6-deoxy-L-ascorbic acid and the 6-deoxy-6-halo-L-ascorbic acid derivatives, which are useful as antioxidants. Accordingly, the present invention also embraces a method for the preparation of a compound of the formula

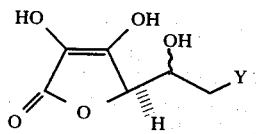

and the salts thereof, by the reaction of a compound of formula I with a nucleophile Y, wherein Y is $H^-$, $-OH$, $N_3^-$, $-CN$, $-SCN$, $-N=C=O$, $Ar-O-$, $Ar-S-$, $R-S-$ or $:NHR_1R_2$, wherein R, $R_1$ and $R_2$ are each alkyl of 1 to 3 carbon atoms and Ar is phenyl.

The salts of the compounds of formulae I, II and III embraced by the present invention include the alkali metal salts, alkaline earth metal salts, ammonium, tetraalkylammonium and trialkylbenzylammonium salts, wherein each alkyl group has from 1 to 8 carbon atoms.

DETAILED DESCRIPTION OF THE INVENTION

The novel intermediates of formula I are readily prepared from the known 6-deoxy-6-halo-L-ascorbic acid and 6-deoxy-6-halo-D-erythorbic acid, or salts thereof (U.S. Pat. No. 4,043,937) by reaction with a base, for example an alkali metal hydroxide, an alkaline earth metal hydroxide, or an alkali metal carbonate or bicarbonate, preferably sodium or potassium carbonate, in aqueous solution at a temperature from about 0° C. to about 40° C., preferably from about 15° C. to about 25° C., at a pH from about 7.5 to about 10, preferably from about 8 to 9. The 5,6-epoxide of formula I formed by this reaction is hydrolytically unstable in aqueous solution, having a half-life at ambient temperatures of approximately 5 hours at a pH of 8 to 9. The intermediate is therefore most conveniently formed in situ and is reacted directly with an appropriate nucleophile to form the compounds of formulae II and III, as hereinafter described. If desired, the 5,6-epoxide of formula I can be isolated as the alkali metal salt, or other salt, by precipitation from the reaction mixture, for example by addition of a non-solvent, such as acetone.

Salts of the compounds of formula I include the alkali metal salts, such as the sodium, potassium and lithium salts, alkaline earth metal salts, such as calcium and magnesium salts, the ammonium, tetraalkylammonium or trialkylbenzylammonium salts, wherein each alkyl group has from 1 to 8 carbon atoms. Such salts may be prepared by conventional methods, for example, from an appropriate salt of the 6-deoxy-6-halo- starting material, or by adding an aqueous solution containing the desired counterion to a solution of the compound of formula I.

The novel compounds of formula I are useful intermediates for the preparation of 6-deoxy-6-substituted-L-ascorbic acid and 6-deoxy-6-substituted-D-erythorbic acid and salts thereof. Thus, both known and novel 6-deoxy-6-substituted-L-ascorbic acid and 6-deoxy-6-substituted-D-erythorbic acid derivatives are readily prepared by reaction of an appropriate 5,6-epoxide of formula I, preferably as the alkali metal salts, preferably formed in situ as previously described, with an appropriate nucleophile Y, wherein Y is as previously defined. The nucleophile Y is the reactive species of readily available nucleophilic reagents, such as phenols, thiophenols, thioalcohols, appropriate alkali metal salts, ammonia, primary and secondary alkyl amines and the like, as will be readily understood by those skilled in the art. Thus, for example, the compound of formula I may be catalytically hydrogenated, for example using a palladium on carbon catalyst, when the nucleophile $H^-$ is the reactive species. Similarly, the reaction of the appropriate compound of formula I with an alkali metal cyanide, azide, isocyanate, cyanate, thiocyanate, and the like, will afford the corresponding compounds of formula III. The reaction of the compound of formula I and the nucleophile Y is generally conducted in aqueous solution, optionally containing an organic cosolvent, such as an alkyl alcohol of 1 to 4 carbon atoms, at a temperature from about 0° C. to about 40° C., preferably about 15° C. to 25° C. As noted previously, the compound of formula I is preferably generated in situ and the reaction with a nucleophile Y to form the compound of III is therefore conveniently effected by the addition of the 6-deoxy-6-halo-L-ascorbic acid or 6-deoxy-6-halo-D-erythorbic acid or a salt thereof to a basic solution of the nucleophile Y. The compound of formula III can be obtained as the free acid by acidification of the reaction medium, for example by addition of a mineral acid such as hydrochloric acid or sulfuric acid, and isolated from the reaction mixture, for example by removal of the solvent under vacuum. Alternatively, the compound of formula III may be isolated from the basic reaction mixture as an appropriate salt, for example by evaporation of the solvent or by addition of a non-solvent such as acetone. The salts can then be converted, if desired, to the corresponding free acid by reaction with an appropriate acid or by use of an ion exchange resin in the hydrogen form. The salts of the compounds of formula III may also be obtained from the free acid, isolated as described above, by reaction with an appropriate base, for example an alkali metal hydroxide, an alkaline earth metal hydroxide, ammonium or tetraalkylammonium hydroxides or an alkali metal carbonate or bicarbonate, and the like.

Preferred novel compounds of this invention, useful as antioxidants, are those of formula II. The compounds where X is azido, phenoxy or thiophenoxy are readily prepared by the reaction of an appropriate 5,6-epoxide of formula I with an alkali metal azide, a phenol, or a thiophenol, respectively, in aqueous solution, as described hereinabove. The compound of formula II wherein X is amino is readily prepared by reduction of the corresponding compound wherein X is azido, for example, by catalytic reduction, for example using a palladium on carbon catalyst in aqueous solution at a temperature from about 20° C. to about 50° C. The compounds of formula II are obtained either as the free acid or an appropriate salt, as described hereinabove.

The compounds of formulae II and III and their salts are effective antioxidants and may be employed to stabilize organic materials subject to oxidation, especially food products, edible oils, fats, waxes, vitamins, flavorings and the like. The antioxidant compound is intimately mixed with the oxidation sensitive substrate, for example by the addition of an aqueous solution or of finely divided solid particles, such that the antioxidant is dispersed throughout the substrate at a concentration from about 10 to 1,000 ppm, preferably about 25 to 200 ppm, based on the weight of the material to be stabilized. A suitable test for evaluation of the antioxidant activity of the compounds of formulae II and III in food stuffs, edible oils and the like, is the Schaal oven test, as described in "Handbook of Food Additives", T. E. Furia, editor, Chemical Rubber Company Press, Cleveland, Ohio, second edition, page 201, 1975.

The compounds of formulae II and III are also effective as inhibitors of nitrosamine formation in meat products containing nitrites, for example, in frankfurters or bacon. The addition of from about 250 to 1000 ppm of a compound of formula II or III to the meat product prior to or during curing is effective to reduce nitrosamine formation. A suitable method to evaluate nitrosamine inhibition in such meat products is that described by Fiddler et al. J. Ag. Food Chem. 26, 653 (1978).

The present invention is illustrated by the following examples. However, the invention is not limited to the specific details of these examples.

EXAMPLE 1

6-Bromo-6-deoxy-L-ascorbic acid

The 6-bromo derivative of L-ascorbic acid was synthesized by the procedure of J. Kiss and K. Berg, U.S. Pat. No. 4,043,937, on a 50 g scale, affording after recrystallization from nitromethane 25 g (38%) of the title compound: mp 175°–176° (lit 175°–176°); $V_{max}^{KBr}$ 5.74 (s), 6.02 (s), $^1$H nmr (DMSO-d$_6$) δ4.83 (d, 1, J=2.0 Hz), 3.93 (m, 1), 3.52 (abx, 2).

EXAMPLE 2

5,6-Anhydro-L-ascorbic acid

To a solution of 1.04 g (8.4 mmol) of sodium carbonate in 6 ml of D$_2$O was added 1.00 g (4.2 mmol) of 6-bromo-L-ascorbic acid in 4 ml of D$_2$O. The reaction was followed by $^1$H-nmr with respect to time. After 30 minutes the reaction mixture consisted of 86% of the 5,6-epoxide of ascorbic acid: $^1$H-nmr (D$_2$O)δ 4.37 (d, 1, J=4.8 Hz), 3.39 (m, 1), 3.02 (abx, 2). Attempts to add the reaction mixture to Dowex 50 and isolate the free acid afforded L-ascorbic acid. Under the basic reaction conditions, the 5,6-epoxide had a t$_{\frac{1}{2}}$ of 4 hours 50 minutes and was converted completely to L-ascorbic acid over a 21 hr period at pH 9.

EXAMPLE 3

6-Deoxy-6-thiophenoxy-L-ascorbic acid

To a solution of 21.6 g (0.174 mol) of sodium carbonate in 100 ml of 75/25 water/methanol was added sequentially 2.7 ml (0.046 mol) of thiophenol and 10.0 g (0.042 mol) of 6-deoxy-6-bromo-L-ascorbic acid. The mixture solidified after stirring for 15 minutes and reliquified after an additional hour. The mixture was allowed to stir for an additional 30 minutes and was acidified to pH 1 with 6 N hydrochloric acid. The acidified solution was extracted with ethyl acetate (3×100 ml) and the combined organic layers dried over sodium sulfate. Removal of solvent in vacuo afforded 8.1 g of crude crystalline thio-ether. Recrystallization from water afforded needles of the title compound: mp 99°–100°; $^1$H-nmr-(DMSO-d$_6$)δ 7.32 (S,5,arom.), 4.75 (d,1, J=1.6 Hz), 3.83 (t, 2, J=7.2 Hz), 3.08 (d, 2,J=3.6 Hz); $^{13}$C-nmr-(DMSO-d$_6$) 170.52, 152.75, 136.04, 129.22, 128.23, 125.93, 118.28, 76.13, 66.71, 35.95; Mass spectrum (70 eV) m/e 268.0389 (C$_{12}$H$_{12}$O$_5$S$_1$, parent) $V_{max}^{KBr}$ 5.71 (s), 6.00 (s).

EXAMPLE 4

6-Deoxy-6-phenoxy-L-ascorbic acid

To a stirred solution of 7.44 g (0.06 mol) sodium carbonate in 25 ml of water was added 4.76 g (0.02 mol) of 6-bromo-L-ascorbic acid in small portions, followed by 3.8 g (0.04 mol) of phenol. The solution thickened to a white mobile paste, gradually turning yellow after stirring 6 hours under a nitrogen atmosphere. The reaction mixture was then adjusted to pH 0.5 with 6 N aqueous hydrochloric acid the aqueous solution extracted with ethyl acetate (3×100 ml), the ethyl acetate layer washed with water, brine and dried over anhydrous magnesium sulfate. On removal of solvent in vacuo the residue was triturated with benzene, the resulting crystals collected by filtration and dried under vacuum overnight affording 1.54 g of crude title compound. A sample for analysis was obtained by recrystallization from nitromethane followed by drying under vacuum overnight: mp 160°–161°; $V_{max}^{KBr}$ 5.68 (s) 6.00 (s); $^1$H-nmr (D$_2$O): 7.54–6.75 (m, 5, arom.), 4.93 (broad s, 1), 7.20 (m, 3, —CH$_2$—O and —CH—OH); mass spectrum (70 eV): m/e 252.0563 (parent, C$_{12}$H$_{12}$O$_6$, 136 (—O—CH$_2$—C$^+$H—OH), 116

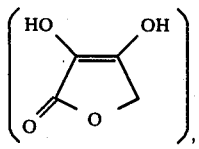

107 (—O$^+$=CH$_2$), 94 (base, —OH); $[\alpha]_D^{24}$ 79.3° (C 1.09, CH$_3$OH).

Anal. Calcd. for C$_{12}$H$_{12}$O$_6$: C, 57.14; H, 4.80. Found: C, 56.77; H, 4.91.

EXAMPLE 5

6-Deoxy-L-ascorbic acid

To a solution of 10.8 g (85 mmol) of sodium carbonate in 100 ml of water was added 10.0 g (42 mmol) of 6-bromo-L-ascorbic acid followed by 2 g of 5% Pd/C. The mixture was hydrogenated in a Parr shaker apparatus at 30 psi hydrogen overnight. After the theoretical uptake of hydrogen, the catalyst was removed by filtration through celite and the filtrate stirred with 100 ml of Dowex 50 ion exchange resin (hydrogen form) for 1 hour. The resin was removed by filtration and washed with 3×100 ml of water. The combined filtrate and washings were treated with 0.5 g of Darco, filtered and the solvent removed in vacuo to an oil. Trituration with ethyl acetate afforded 3.75 g (56%) of a white crystalline solid, 93.3% pure by iodine titration. Recrystallization from ethyl acetate afforded a sample for analysis: mp 162°–163° (lit. 167°–168°);$\gamma_{max}^{KBr}$ 5.80 (s), 6.10 (s); $^1$H-nmr (D$_2$O)$\delta$ 4.83 (d, 1, J=2.0 Hz); 4.15 (quartet of doublets, 1, J=2.0 Hz, J'=6.8 Hz); 1.36 (d, 3, J=6.8 Hz), $[\alpha]_D^{24}$ 39.2° (C 1.02, CH$_3$OH).

Anal. Calc. for C$_6$H$_8$O$_5$: C, 45.01; H, 5.04. Found: C, 44.80; H, 4.97.

EXAMPLE 6

6-Amino-6-deoxy-L-ascorbic acid

To a solution of 15.6 g (126 mmol) of sodium carbonate in 100 ml of water was slowly added 15 g (63 mmol) of 6-bromo-L-ascorbic acid in 20 ml of water followed by 6.0 g (92 mmol) of sodium azide. After stirring overnight, 175 ml of Dowex 50 ion exchange resin (hydrogen form) was added, the slurry stirred another hour, and the resin removed by filtration. After washing the resin exhaustively with water (4×100 ml) the filtrate and washings were concentrated to 150 ml, 3 g of 5% Pd/C added and the mixture, containing the formed 6-azido-6-deoxy-L-ascorbic acid, was hydrogenated in a Parr shaker apparatus at 50 psi hydrogen pressure.

After the theoretical uptake of hydrogen (6 hours), the catalyst was removed by filtration and the filtrate concentrated in vacuo to afford a white amorphorous solid (3.75 g, 95% purity by iodine titration). A sample for analysis was recrystallized from water and dried overnight under vacuum: mp 210° (d); $[\alpha]_D^{23}$ −11.7° (C 0.886, 0.1 N HCl); $[\alpha]_D^{23}$ +91.8° (C 0.687, H$_2$O); $[\alpha]_D^{23}$ +126° (C 0.920, 0.1 N NaOH); UV (H$_2$O) max 258 (A=11.2×10$^4$); UV (0.1 N NaOH) max 294 (A=3.89×10$^4$); UV (0.1 N HCl)$\epsilon$max 236 ($\lambda$=1.8×10$^4$); $V_{max}^{KBr}$ 5.77 (S), 6.25 (S); $^1$H-nmr (D$_2$O, pH 5) 4.33 (broad S, 1), 3.85 (broad t, 1, J=7.0 Hz), 2.79 (broad d, 2, J=7.0 Hz); (D$_2$O, pH 1) 4.94 (d, 1, J=2.0 Hz), 4.28 (8 lines, 1), 3.28 (ABX, 2).

Anal, Calc. for C$_6$H$_9$O$_5$N: C, 41.15; H, 5.18; N, 8.00. Found: C, 40.97; H, 5.15; N, 8.07.

I claim:

1. A salt of a compound of the formula

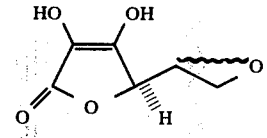

2. A compound of claim 1 wherein said salt is an alkali metal or alkaline earth metal salt.

3. A sodium, potassium, calcium or magnesium salt of 5,6-anhydro-L-ascorbic acid.

4. A sodium, potassium, calcium or magnesium salt of 5,6-anhydro-D-erythorbic acid.

* * * * *